US009616007B2

(12) United States Patent
Herrwerth et al.

(10) Patent No.: US 9,616,007 B2
(45) Date of Patent: Apr. 11, 2017

(54) COMPOSITION COMPRISING MIXTURES OF ISOSTEARAMIDE, GLYCEROL ESTER AND WATER

(75) Inventors: Sascha Herrwerth, Essen (DE); Oliver Springer, Wesel (DE); Ursula Westerholt, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 13/822,133

(22) PCT Filed: Oct. 12, 2011

(86) PCT No.: PCT/EP2011/067774

§ 371 (c)(1), (2), (4) Date: Mar. 11, 2013

(87) PCT Pub. No.: WO2012/062519

PCT Pub. Date: May 18, 2012

(65) Prior Publication Data

US 2013/0171087 A1 Jul. 4, 2013

(30) Foreign Application Priority Data

Nov. 10, 2010 (DE) ........................ 10 2010 043 675
Jan. 26, 2011 (DE) ........................ 10 2011 003 170

(51) Int. Cl.

| | |
|---|---|
| ***A61K 8/42*** | (2006.01) |
| ***A61K 8/37*** | (2006.01) |
| ***A61Q 5/02*** | (2006.01) |
| ***A61Q 5/12*** | (2006.01) |
| ***A61Q 19/10*** | (2006.01) |
| ***A61Q 5/10*** | (2006.01) |
| ***A61Q 19/00*** | (2006.01) |
| *A61Q 5/00* | (2006.01) |

(52) U.S. Cl.

CPC ................ *A61K 8/42* (2013.01); *A61K 8/375* (2013.01); *A61Q 5/02* (2013.01); *A61Q 5/10* (2013.01); *A61Q 5/12* (2013.01); *A61Q 19/00* (2013.01); *A61Q 19/10* (2013.01); *A61K 2800/48* (2013.01); *A61Q 5/006* (2013.01)

(58) Field of Classification Search

CPC ...... A61K 8/42; A61K 8/375; A61K 2800/48; A61Q 5/006; A61Q 5/02; A61Q 5/12; A61Q 19/10; A61Q 5/10; A61Q 19/00

See application file for complete search history.

(56) References Cited

U.S. PATENT DOCUMENTS

| | | | | |
|---|---|---|---|---|
| 5,198,209 | A | 3/1993 | Zhou et al. | |
| 5,407,668 | A * | 4/1995 | Kellner ................ | A61K 8/0229 424/65 |
| 2003/0012759 | A1 | 1/2003 | Bowen-Leaver et al. | |
| 2009/0068255 | A1* | 3/2009 | Yu ........................ | A61K 8/0212 424/450 |

FOREIGN PATENT DOCUMENTS

| | | | |
|---|---|---|---|
| EP | 0 574 277 | A1 | 12/1993 |
| EP | 0786250 | A1 | 7/1997 |
| EP | 1671621 | A1 | 6/2006 |
| FR | 2691472 | A1 | 11/1993 |
| WO | WO 02080864 | A1 | 10/2002 |
| WO | WO 02092740 | A1 | 11/2002 |
| WO | WO 2008003090 | A2 | 1/2008 |

OTHER PUBLICATIONS

Antil® SPA 80 ("Antil", Apr. 2008, Evonik Industries, https://personal-care.evonik.com/product/personal-care/en/products/product-finder/products-of-formulation/Pages/product-details.aspx?pid=38992&csm=1).*
English-language translation of Chinese Office Action issued in related Chinese Patent Application No. CN 201180050542.4
Database GNPD (Online) Mintel: Jul. 2010; "Shampoo Moisturiser"; XP002667298, Database accession No. 1388145.
Database GNPD (Online) Mintel: Jul. 2010; "Active Shampoo Moisturiser"; XP002667299, Database accession No. 1351644.
Database GNPD (Online) Mintel: Jul. 2010; "Hair Loss Schampoo", XP002667300, Database accession No. 1349975.
Database GNPD (Online) Mintel: Feb. 2010; "Neutral Liquid Soap", XP002667301, Database accession No. 1266952.
Database GNPD (Online) Mintel: Sep. 2009; "Aloe Vera Hydrating Shampoo", XP002667302; Database accession No. 1174615.
Database GNPD (Online) Mintel: Apr. 2009; "Anti-Dandruff Hair Loss Shampoo", XP002667303; Database accession No. 1078156.
Database GNPD (Online) Mintel: Dec. 2008; "Hydrating Shampoo", XP002667304; Database accession No. 1021337.
Database GNPD (Online) Mintel: Nov. 2005; "Bath Cermony Cream", XP002667305; Database accession No. 411907.
Database GNPD (Online) Mintel: Feb. 2005; "Shampoo", XP002667306; Database accession No. 10205935.
Database GNPD (Online) Mintel: Jun. 2002; "Gel de Bano Bath Gel", XP002667307; Database accession No. 153865.
Database GNPD (Online) Mintel: Mar. 2002; "Gel Leche Shower Gel", XP002667308; Database accession No. 142931.
Database GNPD (Online) Mintel: Dec. 2002: "Body Wash Dermoprotector", XP002667309; Database accession No. 181470.
International Search Report directed dated Feb. 13, 2012 directed to PCT/EP2011/067774.

* cited by examiner

*Primary Examiner* — Sean Basquill
(74) *Attorney, Agent, or Firm* — Scully, Scott, Murphy & Presser

(57) ABSTRACT

The present invention is directed to compositions comprising a mixture comprising at least one isostearamide, at least one glycerol ester and water, and also to the use of these compositions as thickeners or shampoos, conditioners, shower gels, body cleaning compositions or skin cleaning compositions or for producing shampoos, conditioners, shower gels, body cleaning compositions or skin cleaning compositions.

15 Claims, No Drawings

COMPOSITION COMPRISING MIXTURES OF ISOSTEARAMIDE, GLYCEROL ESTER AND WATER

The present invention is directed to compositions, in particular formulations for the cleaning and care of human or animal body parts, comprising a mixture comprising at least one isostearamide, at least one glycerol ester and water, and also to the use of these compositions as thickeners in cleaning or care formulations, such as e.g. shampoos, conditioners, shower gels, body cleaning compositions or skin cleaning compositions or for producing shampoos, conditioners, shower gels, body cleaning compositions or skin cleaning compositions.

Modern cosmetic cleaning products for skin and/or hair, such as for example shower baths and hair shampoos, usually have the following ingredients:

water (as the most important solvent),
surfactant,
viscosity regulators/thickeners for thickening the formulation,
solubility promoters (solubilizers) for water-insoluble substances,
perfume oils,
preservatives, and
active ingredients for the care of skin and hair, such as e.g. refatting agents Typical thickeners or viscosity regulators used according to the prior art are sodium chloride (NaCl), low molecular weight nonionic surfactants, such as coconut fatty acid monoethanolamide or diethanolamide (Cocamide MEA or DEA) and laureth-3, or polymers, high molecular weight, associative, highly ethoxylated fatty derivatives, such as e.g. PEG-200 hydrogenated glyceryl palmate, PEG-150 distearate and PEG-120 methyl glucose dioleate.

Fatty acid monoethanolamides and fatty acid diethanolamides are used in a large number of applications in the cosmetics industry. Cocamide DEA (commercially available as REWOMID® DC 212 S, Evonik Goldschmidt GmbH) and Cocamide MEA (commercially available as REWOMID® C 212, Evonik Goldschmidt GmbH) are standard thickeners in the industry for aqueous surface-active formulations, such as e.g. hand washing soaps, shower gels and shampoos. Both are characterized by very high thickening effectiveness.

However, both products have disadvantages:

Cocamide DEA is a potential nitrosamine source since a secondary amine is used as raw material during the synthesis.

Cocamide MEA is not a potential source of undesired nitrosamines, but is in the form of a solid at room temperature and therefore has disadvantages upon processing since melting of the raw material and warm processing of the formulation are necessary.

As alternative, hitherto e.g. Isostearamide MIPA (isostearamide of 1-amino-2-propanol, commercially available as REWOMID® SPA, Evonik Goldschmidt GmbH) is known, which is liquid at room temperature and, since it is based on a primary amine as raw material, does not constitute a potential source of undesired nitrosamines in cosmetic formulations. A disadvantage of this raw material is that this liquid raw material has a tendency to separate upon cooling and this separation can only be reversed by heating to 40° C. and stirring. This separation is particularly marked if the product is cooled to below 15° C., which can only be excluded during transit at great expense. Analyses of the separating solids have revealed that linear stearamides and palmitamides of 1-amino-2-propanol are decisively responsible for the separation. However, these linear fatty acids are generally present in technical grades of isostearic acid in small amounts (ca. 2 to 10%).

A user must therefore either process the whole pack at once or homogenize the product e.g. at 40° C. by stirring. Consequently, Isostearamide MIPA does not constitute an alternative which has an advantage over Cocamide MEA.

The object of the present invention was therefore to provide an alternative thickener which does not have the disadvantages of the thickeners known from the prior art. In particular, the thickener should be processable at room temperature without melting and the homogenization step. Preferably, the thickener should also have no separation upon cooling (to 5° C.) and reheating to room temperature (22° C.) and be processable at room temperature as in the first place.

Surprisingly, it has been found that this object is achieved by a composition according to claim 1, which comprises a mixture comprising water, at least one isostearamide and at least one glycerol ester. In particular, it has thus been found that mixtures of Isostearamide MIPA with glycerol esters and water, preferably mixtures of Isostearamide MIPA, glycerol laurate and/or glycerol caprylate/caprate and water, do not have separation tendencies and consequently do not have the weaknesses of Isostearamide MIPA on its own.

The present invention therefore provides compositions, in particular for the cleaning and care of human or animal body parts, preferably skin and hair, comprising a mixture comprising at least one isostearamide, at least one glycerol ester and water. The present invention likewise provides the use of these compositions as thickeners in cleaning or care formulations, such as e.g. shampoos, conditioners, shower gels, body cleaning compositions or skin cleaning compositions or for producing shampoos, conditioners, shower gels, body cleaning compositions or skin cleaning compositions.

The compositions according to the invention comprising at least one isostearamide, at least one glycerol ester and water, preferably comprising exclusively at least one isostearamide, at least one glycerol ester and water, have the advantage that they are homogeneous and clear at room temperature (22° C.). Upon cooling or freezing these compositions and subsequently heating them to room temperature (22° C.), the mixture becomes clear again and costly heating to 40° C. with stirring for homogenization purposes can be avoided.

The compositions according to the invention, comprising mixtures of at least one isostearamide, at least one glycerol ester and water, and further components, also have the advantage that they have a high temperature stability (15-40° C.) of the viscosity compared to formulations using standard commercial thickeners. This is therefore of great importance since the use and storage of e.g. shampoos or shower gels does not always take place at room temperature and without the temperature stability of the viscosity, such formulations may suddenly be water-thin.

A further advantage of the compositions according to the invention is that the compositions, in particular the mixtures present therein, have very good conditioning properties when used on hair. It has surprisingly been found that the mixture both has a conditioning effect even by itself, but also enhances the effect of standard conditioners such as e.g. cationic polymers or silicone derivatives.

A further advantage of the compositions according to the invention is that the compositions, in particular the mixtures present therein, have very good skin-conditioning properties (properties improving the skin feel).

The compositions according to the invention, in particular the mixtures present according to the invention, moreover have the advantage that they have good foam properties. Compositions which also have conventional surfactants besides the mixture lead to considerably better foam properties than do those compositions not according to the invention which do not comprise a mixture present according to the invention.

The compositions according to the invention, in particular the mixtures present in these, moreover have the advantage that they have good solubilizing properties. This property makes it possible in aqueous surface-active compositions according to the invention to dissolve cosmetic oils and/or perfume oils to give a clear solution (thus without the appearance of cloudiness).

A yet further advantage is that the use of the compositions according to the invention, in particular the mixtures present in these, is possible also in polyether-free surface-active formulations as viscosity regulator, care active ingredient, foam booster or solubilizer. This is surprising and a particular advantage since many conventional thickeners such as, for example, NaCl are not effective in polyether-free formulations, and high molecular weight, associative thickeners which have polyether groups cannot be used in polyether-free formulations since otherwise the formulations would no longer be polyether-free.

As a result of the excellent properties of the mixture(s) used in the compositions according to the invention, it is possible to dispense with the use of further thickeners/viscosity regulators and optionally also with the addition of further refatting agents, foam boosters or solubilizers in the formulation selected in each case.

The compositions according to the invention and also their uses are described below by way of example without any intention to limit the invention to these exemplary embodiments. Where ranges, general formulae or compound classes are given below, then these are intended to include not only the corresponding ranges or groups of compounds explicitly mentioned, but also all part ranges and part groups of compounds which can be obtained by removing individual values (ranges) or compounds. Where documents are cited within the context of the present description, then their content, especially as regards the facts in question, should, in its entirety, form part of the disclosure of the present invention. Where average values are stated below, then, unless stated otherwise, these are number-averaged average values. Unless stated otherwise, percentages are given in percent by weight.

The compositions according to the invention are characterized in that they comprise a mixture comprising at least one isostearamide, at least one glycerol ester and water.

As isostearamide, in principle all isostearamides can be used. Preferably, the mixture comprises as isostearamide an amide which is obtained by reacting isostearic acid or isostearic acid esters, such as e.g. methyl isostearate, with 1-amino-2-propanol, monoethanolamine or diethanolamine, preferably with 1-amino-2-propanol. Such an amide is usually referred to as Isostearamide MIPA (INCl name). A particularly suitable isostearamide of this type is available for example from Evonik Goldschmidt GmbH under the name REWOMID® SPA.

The fraction of isostearamide(s) in the mixture is preferably from 50 to 95% by weight, preferably from 70 to 90% by weight, based on the total weight of the mixture.

It may be advantageous if the mixture according to the invention also has amides which are obtained by reacting linear fatty acids, preferably linear fatty acids having 16 or 18 carbon atoms, preferably palmitic acid and/or stearic acid, with 1-amino-2-propanol, monoethanolamine or diethanolamine, preferably with 1-amino-2-propanol. The fraction of these amides based on linear fatty acids in the mixture is preferably from 2 to 10% by weight, based on the sum of isostearamides and amides of linear fatty acids. The linear amides are often present in commercially available isostearamides. The fraction of the amides based on linear fatty acids can be determined e.g. by gas chromatography, e.g. by means of DGF method DGF C-VI 10a.

As glycerol ester, in principle all glycerol esters can be used. The glycerol esters may be mixtures of mono-, di- and triesters of glycerol. Preference is given to using glycerol esters which have a hydroxyl number (OH number, determined in accordance with DIN 53240 (DGF method C-V 2 17a)) of from 200 to 500 mgKOH/g, preferably from 300 to 475. Particular preference is given to using hydrophilic glycerol esters.

As acid component, the glycerol esters preferably have those carboxylic acids which have from 6 to 24, preferably from 8 to 18, particularly preferably from 8 to 12, carbon atoms. Very particularly preferably, the mixture comprises as glycerol ester a glycerol laurate, preferably a glycerol monolaurate, which is available e.g. under the name TEGIN® L 90 from Evonik Goldschmidt GmbH, and/or a glycerol caprylate/caprate, preferably a glycerol monocaprylate/caprate, which is available e.g. under the name IMWITOR® 742 from SASOL Germany GmbH.

The fraction of glycerol ester in the mixture is preferably from 1 to 45% by weight, preferably from 5 to 30% by weight, based on the total weight of the mixture.

The fraction of water in the mixture is preferably from 0.1 to 15% by weight, preferably from 2 to 10% by weight, based on the total weight of the mixture.

It may be advantageous if the composition consists exclusively of the mixture. Preferred compositions of this type have a fraction of water of from 1 to 15% by weight, preferably from 2 to 10% by weight, a fraction of from 1 to 45% by weight, preferably from 5 to 29% by weight, a fraction of isostearamide(s) of from 50 to 95% by weight, preferably from 70 to 90% by weight, based on the total weight of the mixture. Particularly preferred compositions have a fraction of amides based on linear fatty acids in the mixture which is from 2 to 10% by weight, based on the sum of isostearamides and amides of linear fatty acids.

Such a composition comprising only the mixture can be used e.g. as thickener. The mixture can be used in particular for producing compositions for the cleaning and care of human or animal body parts, in particular for producing shampoo, conditioner, shower gel, body cleaning composition or skin cleaning composition.

In a further advantageous embodiment of the composition according to the invention, besides the mixture and/or constituents thereof, these have further constituents. The fraction of the mixture in such a composition is preferably from 0.01 to 10% by weight, preferably 0.1 to 8% by weight and particularly preferably from 0.2 to 5% by weight. The fraction of water in this composition is preferably greater than 35% by weight, preferably from 50 to 98% by weight and particularly preferably from 75 to 95% by weight, based on the total weight of the composition.

The compositions according to the invention can comprise as further components in particular e.g. those which e.g. are selected from the group of surfactants, emollients, emulsifiers, thickeners/viscosity regulators/stabilizers, UV photoprotective filters, antioxidants, hydrotropes (or polyols), solids and fillers, film formers, pearlescent additives, deodorant and antiperspirant active ingredients, insect repellents, self-tanning agents, preservatives, conditioners, perfume (oil)s, dyes, (cosmetic) active ingredients, care additives, superfatting agents, solubility promoters and solvents. Substances which can be used as exemplary representatives of the individual groups are known to the person skilled in the art and can be found for example in the German application DE 102008001788.4. This patent application is hereby incorporated as reference and thus forms part of the disclosure.

As further constituents, besides the mixture, the composition according to the invention preferably has one or more components selected from surfactants, viscosity regulators for thickening the formulation, solubility promoters (solubilizers) for water-insoluble substances, perfume oils, preservatives and active ingredients for the care of skin and/or hair. The fraction of the sum of these components in the formulation is preferably from 3 to 50% by weight, preferably from 5 to 25% by weight.

Preferably, besides the mixture, the compositions according to the invention have, as additional component, surfactants with an anionic, amphoteric and/or zwitterionic structure. Typical examples of mild, i.e. particularly skin-compatible, surfactants are fatty alcohol polyglycol ether sulphates, monoglyceride sulphates, alkyl sulphates, mono- and/or dialkyl sulphosuccinates, fatty acid isethionates, fatty acid sarcosinates, fatty acid taurides, fatty acid glutamates, ether carboxylic acids, alkyl oligoglucosides, fatty acid glucamides, alkylamidobetaines, alkylbetaines and/or protein acid condensates, the latter for example being based on wheat proteins.

Amphoteric surfactants which may be present are e.g. betaines, amphoacetates or amphopropionates, thus e.g. substances such as the N-alkyl-N,N-dimethylammonium-glycinates, for example cocoalkyldimethylammonium glycinate, N-acylaminopropyl-N,N-dimethylammoniumglycinates, for example cocoacylaminopropyldimethyl-ammonium glycinate, and 2-alkyl-3-carboxymethyl-3-hydroxyethylimidazolines having in each case 8 to 18 carbon atoms in the alkyl or acyl group, and also cocoacylaminoethyl hydroxyethylcarboxymethylglycinate.

Ampholytic surfactants which may be present are those surface-active compounds which, apart from a $C_{8/18}$-alkyl or acyl group in the molecule, comprise at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Further examples of ampholytic surfactants are N-cocoalkylaminopropionate, cocoacylaminoethylaminopropionate and $C_{12/18}$-acylsarcosine.

Preferred anionic surfactants are e.g. the salts of various cations (sodium, ammonium or others) of lauryl sulphate, lauryl ether sulphate, myristyl ether sulphate, cocoyl glutamates, lauryl glucose carboxylates etc. Zwitterionic surfactants which may be present in the formulation are e.g. cocamidopropylbetaine or cocoamidopropylsultaine. As amphoteric surfactants, preference is given in particular to amphoacetates such as sodium cocoamphoacetate or disodium cocoamphodiacetate.

Particular preference is given to surfactants or surfactant mixtures which comprise at least one surfactant from the group comprising lauryl ether sulphates, alkyl sulphates, alkyl oligoglucosides, mono- and/or dialkyl sulphosuccinates, alkylamidobetaines or fatty acid sarcosinates.

The fraction of surfactants in the composition according to the invention is preferably at least 2% by weight, preferably from 4 to 20% by weight and particularly preferably from 6 to 18% by weight, based on the total composition.

Within the context of the present invention, solubilizer or solubility promoter is the term used to refer to a substance which is able to bring water-insoluble compounds into solution in aqueous systems to give the clearest possible solution. According to generally accepted opinion, in this process, aggregates such as micelles are formed, in the structures of which the hydrophobic substances have been integrated. The formation of a "microemulsion", i.e. of a thermodynamically stable mixture of water (aqueous solution), an oil (substance immiscible with water) and a solubilizer or solubility promoter is optimal. Typical solubilizers are ethoxylated fatty derivatives.

In the compositions, perfume oils can generally be added for improving the olfactory properties. Acceptance by the consumer plays the most important role here. In addition, it is possibly advantageous to conceal the intrinsic odours of raw materials used with perfume oils. Suitable perfume oils can be found e.g. in the product catalogues of known manufacturers, such as for example Symrise, Frey&Lau or IFF.

It may be advantageous if the composition according to the invention has preservatives. These are usually used for the microbiological stabilization of the formulations. In the case of a contamination, these ingredients are supposed to prevent microbial growth and, in some instances, also kill microbes. Preservatives are described in detail and regulated in official regulations (e.g. EU Cosmetics Ordinance). Compositions according to the invention have preservatives particularly if the compositions have further constituents besides the mixture.

Care active ingredients or emollients which can be used are in particular e.g. isopropyl myristate, ethoxylated glycerol fatty acid esters, such as for example PEG-7 glyceryl cocoate (such as e.g. TEGOSOFT GC® obtainable from Evonik Goldschmidt GmbH), or cationic polymers, such as for example polyquaternium-7. These are also referred to as refatting agents. In the case of skin cleaning, besides the lipophilic dirt, endogenous lipids are also washed away by the surfactants used. This effect is often perceived as unpleasant, the skin feels rough and harsh. The skin is also referred to as "dry", although what is meant here is the absence of lipids.

Particularly preferred compositions according to the invention are free from polyethylene glycol (PEG) and/or derivatives thereof and propylene glycol (PPG) and/or derivatives thereof.

A composition according to the invention which has further constituents besides the mixture may be in particular a shampoo, a conditioner, a shower gel, a body cleaning composition or a skin cleaning composition. Preferably, compositions according to the invention are liquid, cosmetic, dermatological or pharmaceutical body cleaning compositions, in particular shower baths and shower gels, bath formulations, liquid soaps and shampoos, or are used for producing these products/formulations.

The compositions according to the invention can be used in particular as shampoo, conditioner, shower gel, body cleaning composition or skin cleaning composition or for producing one or more of these products.

The compositions according to the invention which, besides the mixture, have one or more further components can preferably be obtained by mixing a composition according to the invention which comprises the mixture described above or preferably consists of this mixture, with a further component preferably by mixing with water and at least one further component which is different from the components present in the mixture. The mixing preferably takes place such that at least sufficient water and optionally the further components specified above are added for the fraction of the water in the overall composition to be greater than 35% by weight.

In the examples listed below, the present invention is described by way of example without any intention to limit the invention, the scope of which arises from the overall description and the claims, to the embodiments specified in the examples.

EXAMPLES

Unless stated otherwise, all of the concentrations in the application examples are given in percent by weight. To produce the compositions, customary formulation processes known to the person skilled in the art were used.

Example 0

Preparation of Mixtures of Isostearamide, Glycerol Esters and Water

Cap01:

160 g of REWOMID® SPA (Evonik Goldschmidt GmbH), 30 g of TEGIN® L 90 (Evonik Goldschmidt GmbH) and 10 g of distilled water were weighed into a three-neck flask with thermometer and reflux condenser and heated to 60° C. with stirring until a homogeneous, clear mixture was obtained. The product was then cooled and 200 g of a pale yellow, clear liquid were obtained.

This resulting mixture was used in the following examples and is referred to below as Cap01.

Cap02:

166 g of REWOMID® SPA (Evonik Goldschmidt GmbH), 30 g of IMWITOR® 742 (Sasol Germany GmbH) and 4 g of distilled water were weighed into a three-neck flask with thermometer and reflux condenser and heated to 60° C. with stirring until a homogeneous, clear mixture was obtained. The product was then cooled and 200 g of a pale yellow, clear liquid were obtained.

This resulting mixture was used in the following examples and is referred to below as Cap02.

Cap03:

166 g of REWOMID® SPA (Evonik Goldschmidt GmbH), 30 g of glycerol monocaprylate/caprate, which has itself been prepared by reacting 1 mol of glycerol and 1 mol of caprylic/capric acid (PRIFRAC 2912 from Croda), and 4 g of distilled water were weighed into a three-neck flask with thermometer and reflux condenser and heated to 60° C. with stirring until a homogeneous, clear mixture was obtained. The product was then cooled and 200 g of a pale yellow, clear liquid were obtained.

This resulting mixture was used in the examples below and is referred to below as Cap03.

Example 1

Testing the Thickening Properties

The thickening effect of Cap01 from Example 0 was tested against customary surface-active thickeners in various surfactant systems. The viscosity was measured using a Brookfield viscometer (Brookfield LVF, spindle 3, 5 rpm) at 25° C.

Example 1.1

Surfactant System 1a

32% by weight of sodium lauryl ether sulphate (Cognis, Texapon® NSO, 28% strength) and 9% by weight of sodium cocoamphoacetate (Evonik Goldschmidt GmbH, Rewoteric® AM C, 32% strength) was adjusted to a viscosity of 3500 mPas at 25° C. The thickener concentration required for this in each case is shown in Table 1-1. It is found that Cap01 (Example 1.1a) is the most effective compared to standard commercial thickeners not accordance with the invention (Examples 1.1b and 1.1c) since the lowest use concentration is required.

TABLE 1-1

Thickening effect of Cap01 compared to standard commercial thickeners (data in % by wt.)

| | Example | | |
|---|---|---|---|
| | 1.1a | 1.1b | 1.1c |
| Texapon ® NSO (Cognis, INCI: Sodium Laureth Sulfate, 28% strength) | 32.0 | 32.0 | 32.0 |
| Rewoteric ® AM C (Evonik Goldschmidt GmbH, INCI: Sodium Cocoamphoacetate, 32% strength) | 9.0 | 9.0 | 9.0 |
| Cap01 | 1.2 | | |
| REWOMID ® DC 212 S (Evonik Goldschmidt GmbH, INCI: Cocamide DEA) * | | 3.6 | |
| REWOMID ® C 212, (Evonik Goldschmidt GmbH, INCI: Cocamide MEA) * | | | 2.0 |
| Water, demineralized | | ad 100.0 | |
| Viscosity [mPas] | | 3500 | |

Example 1.2

Surfactant System 1b 17.9% by weight of sodium lauryl ether sulphate (Cognis, Texapon® NSO, 28% strength), 6.6% by weight of cocamidopropylbetaine (Evonik Goldschmidt GmbH, TEGO® Betain F 50, 38% strength) and 6.3% by weight of disodium laureth sulphosuccinate (Evonik Goldschmidt GmbH, Rewopol® SB FA 30 B, 40% strength) was adjusted to a viscosity of 3500 mPas at 25° C. This composition is a mild surfactant formulation that is difficult to thicken.

Tab. 1-2 shows what use concentration of the standard commercial thickener not according to the invention (Example 1.2b) REWOMID® DC 212 S (Evonik Goldschmidt GmbH, INCl: Cocamide DEA) was required compared to the mixture Cap01 (Example 1.2a). It is obvious that the mixture Cap01 has a considerably higher effectiveness. In addition, the standard commercial thickener REWOMID® C 212 (Evonik Goldschmidt GmbH, INCl: Cocamide MEA) was also tested in this surfactant system, with no adequate thickening and clouding being observed. Cocamide MEA can therefore not be used as thickener in this surfactant system.

TABLE 1-2

Thickening effect of Cap01 in a mild, difficult-to-thicken formulation compared to standard commercial thickeners (data in % by wt.)

| | Example | |
|---|---|---|
| | 1.2a | 1.2b |
| Texapon ® NSO (Cognis, INCI: Sodium Laureth Sulfate, 28% strength) | 17.9 | 17.9 |
| Rewopol ® SB FA 30 B(Evonik Goldschmidt GmbH, INCI: Disodium Laureth Sulfosuccinate, 40% strength) | 6.3 | 6.3 |
| TEGO ® Betain F 50 (Evonik Goldschmidt GmbH, INCI: Cocamidopropyl Betaine, 38% strength) | 6.6 | 6.6 |
| NaCl | 1 | 1 |
| Cap01 | 1.7 | |
| REWOMID ® DC 212 S (Evonik Goldschmidt GmbH, INCI: Cocamide DEA) | | 3.8 |
| Water, demineralized | ad 100.0 | |
| Viscosity [mPas], | 3500 | |

Example 1.3

Temperature Dependency of the Viscosity in Surfactant System 1c

32% by weight of sodium lauryl ether sulphate (Cognis, Texapon® NSO, 28% strength), 8% by weight of cocamidopropylbetaine (Evonik Goldschmidt GmbH, TEGO® Betain F 50, 38% strength) and 0.7% by weight of NaCl were adjusted to a viscosity of 4200 mPas at 25° C. The thickener concentration required for this purpose in each case is shown in Table 1-3, with a thickener according to the invention being used in Example 1.3a and standard commercial thickeners not according to the invention being used in Examples 1.3b and 1.3c. The compositions were then heated at 40° C. for 12 hours and the viscosities of the compositions were measured again. It was observed that the composition has the highest temperature stability when using Cap01.

TABLE 1-3

Temperature stability of the viscosity of compositions using Cap01 compared to standard commercial thickeners (data in % by wt.)

| | Example | | |
|---|---|---|---|
| | 1.3a | 1.3b | 1.3c |
| Texapon NSO ® (Cognis, INCI: Sodium Laureth Sulfate, 28% strength) | 32.0 | 32.0 | 32.0 |
| TEGO ® Betain F 50 (Evonik Goldschmidt GmbH, INCI: Cocamidopropyl Betaine, 38% strength) | 8.0 | 8.0 | 8.0 |
| Cap01 | 1.0 | | |
| REWOMID ® DC 212 S (Evonik Goldschmidt GmbH, INCI: Cocamide DEA) | | 1.6 | |
| REWOMID ® C 212 (Evonik Goldschmidt GmbH, INCI: Cocamide MEA) | | | 1.0 |
| NaCl | 0.7 | 0.7 | 0.7 |
| Water, demineralized | | ad 100.0 | |
| Viscosity [mPas] at 25° C. | 4200 | 4200 | 4200 |
| Viscosity [mPas] at 40° C. | 3100 | 500 | 200 |

Example 1.4

Temperature Dependency of the Viscosity in Surfactant System 1b

The formulations with surfactant system 1b (see Table 1-2) were likewise heated overnight to 40° C. and the viscosities were determined again (Table 1-4). It was observed that the composition has the highest temperature stability when using Cap01.

TABLE 1-4

Temperature stability of the viscosity of compositions using Cap01 compared to REWOMID ® DC 212 S (Evonik Goldschmidt GmbH, INCI: Cocamide DEA). Data in % by wt.

| | Example | |
|---|---|---|
| | 1.4a | 1.4b |
| Texapon ® NSO (Cognis, INCI: Sodium Laureth Sulfate, 28% strength) | 17.9 | 17.9 |
| Rewopol ® SB FA 30 B(Evonik Goldschmidt GmbH, INCI: Disodium Laureth Sulfosuccinate, 40% strength) | 6.3 | 6.3 |
| TEGO ® Betain F 50 (Evonik Goldschmidt GmbH, INCI: Cocamidopropyl Betaine, 38% strength) | 6.6 | 6.6 |
| NaCl | 1 | 1 |
| Cap01 | 1.7 | |
| REWOMID ® DC 212 S (Evonik Goldschmidt GmbH, INCI: Cocamide DEA) | | 3.8 |
| Water, demineralized | ad 100.0 | |
| Viscosity [mPas] at 25° C. | 3500 | 3500 |
| Viscosity [mPas] at 40° C. | 2800 | 450 |

Example 2

Testing the Conditioning of Skin (Skincare Performance) and Foam Properties by Means of a Handwashing Test To assess the refatting care of skin (skincare performance) and the foam properties of Cap01 in aqueous, surface-active compositions (surfactant formulations), sensory handwashing tests were carried out against the market standard polyethylene glycol(7) glyceryl monoacetate. Polyethylene glycol(7) glyceryl monococoate is widespread in the industry as a refatting care active ingredient and is considered to be a highly effective component in aqueous, surface-active formulations.

A group consisting of 10 trained test personnel washed their hands in a defined manner and assessed foam properties and skin feel by reference to a grading scale from 1 (poor) to 5 (very good). The products used were tested in each case in a standardized surfactant formulation (Table 2-1).

As control formulation 2a, a surfactant formulation without the addition of an additive is used. The surfactant formulation 2b is the composition according to the invention and the surfactant formulation 2c is a composition not in accordance with the invention (Table 2-1).

TABLE 2-1

Test formulations for handwashing test according to Example 2.1 (data in % by wt.)

| | Formulation examples | | |
|---|---|---|---|
| | 2a | 2b | 2c |
| Texapon NSO ® (Cognis, INCI: Sodium Laureth Sulfate, 28% strength) | 32 | 32 | 32 |
| TEGO ® Betain F 50 (Evonik Goldschmidt GmbH INCI: Cocamidopropyl Betaine, 38% strength) | 8 | 8 | 8 |
| NaCl | 1.5 | 1.5 | 1.5 |
| Water, demineralized | | ad 100 | |
| Cap01 | | 1.0 | |

TABLE 2-1-continued

Test formulations for handwashing test according to Example 2.1 (data in % by wt.)

| | Formulation examples | | |
|---|---|---|---|
| | 2a | 2b | 2c |
| Tegosoft ® GC (Evonik Goldschmidt GmbH, INCI: Polyethylene glycol(7) glyceryl monococoate) | | | 1.0 |

Table 2-2 shows the results of the handwashing test. By reference to the measurement results, it is clear that the composition 2b according to the invention using Cap01 brings about a better skin smoothness and skin softness 3 minutes after application and a superior skin feel during washing compared to the comparison compositions 2a and 2c according to the prior art. Furthermore, by reference to the measurement values, it is clear that the composition 2b according to the invention with Cap01 brings about an improvement in foam properties relative to the compositions according to the prior art.

TABLE 2-2

Results of the handwashing test according to Example 2.1

| | Test formulation | | |
|---|---|---|---|
| | 2a | 2b | 2c |
| Foaming behaviour | 2.65 | 3.95 | 3.0 |
| Foam volume | 2.75 | 3.3 | 3.1 |
| Foam creaminess | 2.75 | 3.25 | 3.15 |
| Skin smoothness after 3 min | 2.95 | 3.95 | 3.65 |
| Sin softness after 3 min | 3.1 | 4.1 | 3.35 |

Example 3

Testing the Solubilizing Properties

The solubilizing properties of Cap01 were tested by dissolving the water-insoluble oil isopropyl myristate (Evonik Goldschmidt GmbH, TEGOSOFT® M) in a surfactant solution consisting of 40% by weight of sodium lauryl ether sulphate (Cognis, Texapon® NSO, 28% strength), 10% by weight of cocamidopropylbetaine (Evonik Goldschmidt GmbH, TEGO® Betain F 50, 38% strength) and 0.5% by weight of solubilizer additive (see Examples 3.3, 3.4, 3.6 and 3.7) to give a clear solution. For comparison, the oil was dissolved in the pure surfactant solution (see Examples 3.1 and 3.2 in Table 3-1) without the addition of solubilizer. As market standard PEG-7 Glyceryl Cocoate (Evonik Goldschmidt GmbH, TEGOSOFT® GC) (see Examples 3.6, 3.7 and 3.8 in Table 3-1) was used.

Table 3-1 gives the amount of isopropyl myristate (Evonik Goldschmidt GmbH, TEGOSOFT® M) which could still be dissolved to give a clear solution in the particular system. Above this amount, cloudiness results.

TABLE 3-1

Formulations and results - solubilization experiments (data in % by wt.)

| | Example | | | | | | | |
|---|---|---|---|---|---|---|---|---|
| | 3.1 | 3.2 | 3.3 | 3.4 | 3.5 | 3.6 | 3.7 | 3.8 |
| Texapon ® NSO (Cognis, INCI: Sodium Laureth Sulfate, 28% strength) | 40 | 40 | 40 | 40 | 40 | 40 | 40 | 40 |
| TEGO ® Betain F 50 (Evonik Goldschmidt GmbH, INCI: Cocamidopropyl Betaine, 38% strength) | 10 | 10 | 10 | 10 | 10 | 10 | 10 | 10 |
| TEGOSOFT ® M (Evonik Goldschmidt GmbH, INCI: Isopropyl Myristate) | 0.5 | 0.6 | 1.0 | 1.7 | 1.8 | 1.0 | 1.1 | 1.2 |
| Cap01 | | | 0.5 | 0.5 | 0.5 | | | |
| TEGOSOFT ® GC (Evonik Goldschmidt GmbH, INCI: PEG-7 Glyceryl Cocoate) | | | | | | 0.5 | 0.5 | 0.5 |
| Water | | | | ad 100.0 | | | | |
| Appearance | clear | cloudy | clear | clear | cloudy | clear | clear | cloudy |

It can be deduced from the results given in Table 3-1 that Cap01 exhibits a clear solubilizing effect which exceeds the market standard PEG-7 Glyceryl Cocoate (Evonik Goldschmidt GmbH, TEGOSOFT® GC).

Example 4

Testing the Conditioning of Hair by Means of Sensory Tests

For the applications-related assessment of the conditioning of hair, the mixture Cap01 according to the invention was used in simple shampoo formulations. The application properties upon use in a shampoo were tested in the formulations given in Table 4-1.

Examples 4.1 and 4.3 are comparative examples.

TABLE 4-1

Shampoo formulations for testing the hair-conditioning properties of the mixture Cap01 (data in % by wt.)

| | Formulation examples | | | |
|---|---|---|---|---|
| | 4.1 | 4.2 | 4.3 | 4.4 |
| Texapon NSO ®, 28% strength, Cognis (INCI: Sodium Laureth Sulfate) | 32 | 32 | 32 | 32 |

TABLE 4-1-continued

| Shampoo formulations for testing the hair-conditioning properties of the mixture Cap01 (data in % by wt.) | | | | |
|---|---|---|---|---|
| | Formulation examples | | | |
| | 4.1 | 4.2 | 4.3 | 4.4 |
| TEGO ® Betain F 50, 38% strength, Evonik Goldschmidt GmbH (INCI: Cocamidopropyl Betaine) | 8 | 8 | 8 | 8 |
| Jaguar 162, Rhodia (INCI: Guar Hydroxypropyl trimonium Chloride; cationic polymer for improving the effectiveness of conditioners) | | | 0.3 | 0.3 |
| Water, demineralized | ad 100.0 | | | |
| Citric acid | ad pH 6.0 | | | |
| Mixture Cap01 | | 0.5 | | 0.5 |

In the case of the property testing of hair rinses, the pretreatment of the hair takes place by a shampoo which does not contain any conditioners.

For the applications-related assessment, hair tresses which are used for sensory tests are predamaged in a standardized manner by a permanent wave treatment and a bleaching treatment. For this, customary styling products are used. The test procedure, the base materials used and also the details of the assessment criteria are described in DE 103 27 871.

Standardized Treatment of Predamaged Hair Tresses with Conditioning Samples

The predamaged hair tresses, as described above, were treated as follows with the shampoo described above: the hair tresses were wetted under warm running water. The excess water was gently squeezed out by hand, then the shampoo was applied and gently worked into the hair (1 ml/hair tress (2 g)). After a residence time of 1 min, the hair was rinsed for 1 min.

Assessment Criteria:

The sensory evaluations were made using grades which are awarded on a scale from 1 to 5, with 1 being the poorest evaluation and 5 being the best evaluation. The individual test criteria were in each case given their own assessment. The test criteria were: wet combability, wet feel.

Table 4-2 below compares the results of the sensory assessment of the treatment of the hair tresses carried out as described above with the formulations 4.2 and 4.4 according to the invention, and of the comparison formulations 4.1 and 4.3.

TABLE 4-2

| Results of the conditioning of hair from shampoo formulation | | |
|---|---|---|
| | Wet combability | Wet feel |
| Comparison formulation 4a1 | 2.0 | 1.9 |
| Formulation according to the invention 4a2 | 3.0 | 3.1 |
| Comparison formulation 4a3 | 3.1 | 3.1 |
| Formulation according to the invention 4a4 | 3.9 | 3.6 |

Surprisingly, the results show that the compositions according to the invention (formulations 4.2 and 4.4) with the mixture Cap01 are given significantly better evaluations than the corresponding comparison formulations 4.1 and 4.3 without the addition of the mixture Cap01. It could thus be shown that the mixture Cap01, both in formulations which contain no other conditioning compounds (compare 4.1 to 4.2), and also in formulations which contain guar quat as base conditioner (compare 4.3 to 4.4), has a conditioning effect.

The examples given thus demonstrate the care, foam-promoting, conditioning and/or solubilizing effect of the composition Cap01 according to the invention. In addition, the high effectiveness of the composition Cap01 as thickener in various surfactant systems was shown, with the effectiveness of the comparison substances (market standards) sometimes being clearly exceeded. Furthermore, the high viscosity/temperature stability of the compositions with the mixture Cap01 as thickener in various surfactant systems was shown, with the effectiveness of the comparison substances according to the prior art being considerably exceeded.

Example 5

Further Formulation Examples

The formulation Examples 1 to 28 given in Tables 5-1 to 5-28 below show exemplary representatives of a large number of possible compositions according to the invention.

If the preparation of the formulation requires the separate preparation and/or mixing of formulation constituents beforehand, this is referred to as multiphase preparation.

If a two-phase preparation is required, the two phases are characterized as A and B in the tables given. In the case of three-phase processes, the three phases are named as A, B and C. Unless stated otherwise, the data in Tables 5-1 to 5-28 are data in % by wt.

TABLE 5-1

| Formulation Example 1, shampoo, PEG- and sulphate-free | |
|---|---|
| REWOTERIC ® AMC, Evonik Goldschmidt GmbH, 32% strength, (INCI: Sodium Cocoamphoacetate) | 15.00 |
| REWOPOL ® SB F 12 P, Evonik Goldschmidt GmbH, 96% strength, (INCI: Disodium Lauryl Sulfosuccinate) | 3.80 |
| Cap01 | 0.50 |
| Perfume | 0.30 |
| Water | 66.10 |
| TEGO ® Betain F 50, Evonik Goldschmidt GmbH, 38% strength, (INCI: Cocamidopropyl Betaine) | 13.00 |
| ANTIL ® HS 60, Evonik Goldschmidt GmbH, (INCI: Cocamidopropyl Betaine; Glyceryl Laurate) | 1.00 |
| Citric Acid, 30% strength | q.s. |
| Preservative | 0.30 |

TABLE 5-2

| Formulation Example 2, mild hair and body cleaning composition | |
|---|---|
| Plantacare ® 1200 UP, Cognis, 50% strength, (INCI: Lauryl Glucoside) | 11.40 |
| Plantacare ® 818 UP, Cognis, 51% strength, (INCI: Coco Glucoside) | 5.60 |
| Water | 63.00 |
| Cap02 | 0.50 |
| TEGOSOFT ® LSE 65 K SOFT, Evonik Goldschmidt GmbH, (INCI: Sucrose Cocoate) | 1.50 |
| TEGO ® Betain F 50, Evonik Goldschmidt GmbH, 38% strength, (INCI: Cocamidopropyl Betaine) | 18.00 |
| Perfume, preservative | q.s. |
| Citric Acid, 30% strength | q.s. |

TABLE 5-3

| Formulation Example 3, moisturizing skin cleaning composition | | |
|---|---|---|
| A | TEXAPON ® NSO, Cognis, 28% strength, (INCI: Sodium Laureth Sulfate) | 30.00 |
| | Cap03 | 0.70 |
| | Perfume | 0.30 |
| B | Water | 55.40 |
| | TEGOCEL ® fluid HPM 4000, Evonik Goldschmidt GmbH, (INCI: Hydroxypropyl Methylcellulose) | 1.20 |
| | TEGO ® Betain C 60, Evonik Goldschmidt GmbH, 46% strength, (INCI: Cocamidopropyl Betaine) | 8.10 |
| | TEGOSOFT ® APM, Evonik Goldschmidt GmbH, (INCI: PPG-3 Myristyl Ether) | 1.00 |
| | TEGO ® Pearl N 300, Evonik Goldschmidt GmbH, (INCI: Glycol Distearate; Laureth-4; Cocamidopropyl Betaine) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.00 |
| | Preservative | 0.60 |
| | Citric Acid, 30% strength | q.s. |

TABLE 5-4

| Formulation Example 4, clear shower gel | |
|---|---|
| Cap01 | 1.00 |
| TAGAT ® CH 40, Evonik Goldschmidt GmbH, (INCI: PEG-40 Hydrogenated Castor Oil) | 2.50 |
| Perfume | 0.30 |
| TEXAPON ® NSO, Cognis, 28% strength, (INCI: Sodium Laureth Sulfate) | 42.90 |
| Water | 39.30 |
| TEGO ® Betain F 50, Evonik Goldschmidt GmbH, 38% strength, (INCI: Cocamidopropyl Betaine) | 10.70 |
| LACTIL ®, Evonik Goldschmidt GmbH, (INCI: Sodium Lactate; Sodium PCA; Glycine; Fructose; Urea; Niacinamide; Inositol; Sodium benzoate; Lactic Acid) | 1.00 |
| ANTIL ® 171, Evonik Goldschmidt GmbH, (INCI: PEG-18 Glyceryl Oleate/Cocoate) | 2.00 |
| Preservative | 0.30 |

TABLE 5-5

| Formulation Example 5, clear shower gel | |
|---|---|
| TEXAPON ® NSO, Cognis, 28% strength, (INCI: Sodium Laureth Sulfate) | 37.00 |
| Cap02 | 1.00 |
| Perfume | 0.30 |
| Water | 42.00 |
| REWOTERIC ® AMC, Evonik Goldschmidt GmbH, 32% strength, (INCI: Sodium Cocoamphoacetate) | 9.00 |
| TEGO ® Betain 810, Evonik Goldschmidt GmbH, 38% strength, (INCI: Capryl/Capramidopropyl Betaine) | 7.60 |
| LACTIC ®, Evonik Goldschmidt GmbH, (INCI: Sodium Lactate; Sodium PCA; Glycine; Fructose; Urea; Niacinamide; Inositol; Sodium benzoate; Lactic Acid) | 1.00 |
| Citric Acid, 30% strength | 1.30 |
| REWODERM ® LI S 80, Evonik Goldschmidt GmbH, (INCI: PEG-200 Hydrogenated Glyceryl Palmate; PEG-7 Glyceryl Cocoate) | 0.50 |
| Preservative | 0.30 |

TABLE 5-6

| Formulation Example 6, shampoo, PEG- and sulphate-free | |
|---|---|
| REWOTERIC ® AM C, Evonik Goldschmidt GmbH, 32% strength, (INCI: Sodium Cocoamphoacetate) | 15.00 |
| Plantapon ACG 50, Cognis (INCI: Disodium Cocoyl Glutamate) | 3.80 |
| Cap01 | 1.00 |
| Perfume | 0.30 |
| Water | 66.30 |
| TEGO ® Betain F 50, Evonik Goldschmidt GmbH, 38% strength, (INCI: Cocamidopropyl Betaine) | 10.00 |
| VARISOFT ® PATC, Evonik Goldschmidt GmbH, (INCI: Palmitamidopropyltrimonium Chloride) | 2.30 |
| REWOMID ® SPA, Evonik Goldschmidt GmbH, (INCI: Isostearamide MIPA) | 1.00 |
| Preservative | 0.30 |
| Citric Acid, 30% strength | q.s. |

TABLE 5-7

| Formulation Example 7, shower gel | |
|---|---|
| TEXAPON ® NSO, Cognis, 28% strength (INCI: Sodium Laureth Sulfate) | 15.00 |
| Cap03 | 0.50 |
| Perfume | 0.30 |
| PGFAC-S, Cognis (INCI: Sodium cocoyl hydrolyzed wheat protein glutamate) | 1.50 |
| REWOPOL SB CS 50 B, Evonik Goldschmidt GmbH, 40% strength, (INCI: Disodium PEG-5 Laurylcitrate Sulfosuccinate; Sodium Laureth Sulfate) | 7.50 |
| Water | 60.10 |
| TEGO ® Betain F 50, Evonik Goldschmidt GmbH, 38% strength, (INCI: Cocamidopropyl Betaine) | 9.00 |
| TEGO ® Betain 810, Evonik Goldschmidt GmbH, 38% strength, (INCI: Capryl/Capramidopropyl Betaine) | 4.00 |
| ANTIL ® 200, Evonik Goldschmidt GmbH, (INCI: PEG-200 Hydrogenated Glyceryl Palmate; PEG-7 Glyceryl Cocoate) | 1.80 |
| Preservative | 0.30 |

TABLE 5-8

| Formulation Example 8, shampoo, PEG- and sulphate-free | | |
|---|---|---|
| A | REWOTERIC ® AMC, Evonik Goldschmidt GmbH, 32% strength, (INCI: Sodium Cocoamphoacetate) | 20.00 |
| | REWOPOL ® SB F 12 P, Evonik Goldschmidt, 96% strength, (INCI: Disodium Lauryl Sulfosuccinate) | 5.90 |
| | Cap01 | 0.70 |
| B | Water | 66.20 |
| | Citric Acid, 30% strength | 3.60 |
| C | ANTIL ® HS 60, Evonik Goldschmidt GmbH, (INCI: Cocamidopropyl Betaine; Glyceryl Laurate) | 3.00 |
| | Preservative | 0.60 |

TABLE 5-9

| Formulation Example 9, body cleaning composition | | |
|---|---|---|
| A | TEXAPON ® NSO, Cognis, 28% strength, (INCI: Sodium Laureth Sulfate) | 30.00 |
| | Cap01 | 0.50 |
| | ABIL ® B 8832, Evonik Goldschmidt GmbH, (INCI: Bis-PEG/PPG-20/20 Dimethicone) | 0.30 |
| | Perfume | 0.30 |
| B | Water | 53.00 |
| | TEGOCEL ® fluid HPM 4000, Evonik Goldschmidt GmbH, (INCI: Hydroxypropyl Methylcellulose) | 1.20 |
| | Citric Acid Monohydrate | 0.50 |
| | REWOTERIC ® AM C, Evonik Goldschmidt GmbH, 32% strength, (INCI: Sodium Cocoamphoacetate) | 10.00 |
| | TEGO ® Pearl N 300, Evonik Goldschmidt GmbH, (INCI: Glycol Distearate; Laureth-4; Cocamidopropyl Betaine) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.60 |
| | Preservative | 0.60 |
| | Citric Acid, 30% strength | q.s. |

TABLE 5-10

| Formulation Example 10, sprayable hair milk, PEG-free | | |
|---|---|---|
| A | Water | 95.30 |
| | Lactic Acid, 80% strength | 0.40 |
| B | TEGO ® AMID S 18, Evonik Goldschmidt GmbH, (INCI: Stearamidopropyl Dimethylamine) | 1.20 |
| | TEGIN ® G 1100 Pellets, Evonik Goldschmidt GmbH, (INCI: Glycol Distearate) | 0.60 |
| | TEGO ® Care PS, Evonik Goldschmidt GmbH, (INCI: Methyl Glucose Sesquistearate) | 1.20 |
| | TEGOSOFT ® DEC, Evonik Goldschmidt GmbH, (INCI: Diethylhexyl Carbonate) | 0.30 |
| | Cap01 | 1.00 |
| | Perfume, preservative | q.s. |

TABLE 5-11

| Formulation Example 11, body cleansing foam | |
|---|---|
| TEXAPON ® NSO, Cognis, 28% strength (INCI: Sodium Laureth Sulfate) | 14 |
| Perfume | 0.3 |
| Cap01 | 0.2 |
| REWOTERIC ® AM C, Evonik Goldschmidt GmbH, 32% strength (INCI: Sodium Cocoamphoacetate) | 8 |
| Water | 75.5 |
| TEGOCEL ® HPM 50, Evonik Goldschmidt GmbH (INCI: Hydroxypropyl Methylcellulose) | 0.5 |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1 |
| Citric Acid Monohydrate | 0.5 |

TABLE 5-12

| Formulation Example 12, clear conditioning shampoo | |
|---|---|
| TEXAPON ® NSO, Cognis, 28% strength (INCI: Sodium Laureth Sulfate) | 32.00 |
| VARISOFT ® PATC, Evonik Goldschmidt GmbH (INCI: Palmitamidopropyltrimonium Chloride) | 1.50 |
| REWODERM ® LI S 80, Evonik Goldschmidt GmbH (INCI: PEG-200 Hydrogenated Glyceryl Palmate; PEG-7 Glyceryl Cocoate) | 2.00 |
| Cap01 | 0.50 |
| Perfume | 0.25 |
| Water | 54.05 |
| TEGO ® Cosmo C 100, Evonik Goldschmidt GmbH, (INCI: Creatine) | 1.00 |
| Jaguar C-162, Rhodia (INCI: Hydroxypropyl Guar Hydroxypropyltrimonium Chloride) | 0.20 |
| TEGO ® Betain F 50, Evonik Goldschmidt GmbH, 38% strength (INCI: Cocamidopropyl Betaine) | 8.00 |
| NaCl | 0.50 |
| Preservative | q.s. |

TABLE 5-13

| Formulation Example 13, pearlized shampoo | |
|---|---|
| TEXAPON ® NSO, Cognis, 28% strength (INCI: Sodium Laureth Sulfate) | 32.00 |
| Cap01 | 0.50 |
| Perfume | 0.25 |
| Water | 55.25 |
| TEGO ® Betain F 50, Evonik Goldschmidt GmbH, 38% strength (INCI: Cocamidopropyl Betaine) | 8.00 |
| TEGO ® Pearl N 300, Evonik Goldschmidt GmbH (INCI: Glycol Distearate; Laureth-4; Cocamidopropyl Betaine) | 2.00 |
| ANTIL ® 171, Evonik Goldschmidt GmbH (INCI: PEG-18 Glyceryl Oleate/Cocoate) | 1.50 |
| NaCl | 0.50 |
| Preservative | q.s. |

TABLE 5-14

| Formulation Example 14, rinse-off conditioner | |
|---|---|
| Water | 90.20 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| Cap01 | 0.80 |
| TEGO ® Alkanol 1618, Evonik Goldschmidt GmbH (INCI: Cetearyl Alcohol) | 5.00 |
| Preservative, Perfume | q.s. |

TABLE 5-15

| Formulation Example 15, clear conditioning shampoo | |
|---|---|
| TEXAPON ® NSO, Cognis, 28% strength (INCI: Sodium Laureth Sulfate) | 32.00 |
| ANTIL ® 200, Evonik Goldschmidt GmbH (INCI: PEG-200 Hydrogenated Glyceryl Palmate; PEG-7 Glyceryl Cocoate) | 2.00 |
| Cap01 | 1.00 |
| Perfume | 0.25 |
| Water | 56.25 |
| Polymer JR 400, Amerchol (INCI: Polyquaternium-10) | 0.20 |
| TEGO ® Betain F 50, Evonik Goldschmidt GmbH, 38% strength (INCI: Cocamidopropyl Betaine) | 8.00 |
| NaCl | 0.30 |
| Preservative | q.s. |

TABLE 5-16

| Formulation Example 16, moisturizing skin cleaning composition | | |
|---|---|---|
| A | TEXAPON ® NSO, Cognis, 28% strength, (INCI: Sodium Laureth Sulfate) | 30.00 |
| | Cap01 | 0.70 |
| | Perfume | 0.30 |
| B | Water | 56.10 |
| | TEGOCEL ® fluid HPM 4000, Evonik Goldschmidt GmbH, (INCI: Hydroxypropyl Methylcellulose) | 1.20 |
| | TEGO ® Betain C 60, Evonik Goldschmidt GmbH, 46% strength, (INCI: Cocamidopropyl Betaine) | 8.10 |
| | TEGOSOFT ® APM, Evonik Goldschmidt GmbH, (INCI: PPG-3 Myristyl Ether) | 1.00 |
| | Cutina TS, Cognis (INCI: PEG-3 Distearate) | 1.00 |
| | REWODERM ® LI S 80, Evonik Goldschmidt GmbH, (INCI: PEG-200 Hydrogenated Glyceryl Palmate; PEG-7 Glyceryl Cocoate) | 1.00 |
| | Preservative | 0.60 |
| | Citric Acid, 30% strength | q.s. |

TABLE 5-17

| Formulation Example 17, shower gel | |
|---|---|
| TEXAPON ® NSO, Cognis, 28% strength (INCI: Sodium Laureth Sulfate) | 15.00 |
| Cap01 | 0.50 |
| Perfume | 0.30 |
| PGFAC-S, Cognis (INCI: Sodium cocoyl hydrolyzed wheat protein glutamate) | 1.50 |
| REWOPOL SB CS 50 B, Evonik Goldschmidt GmbH, 40% strength, (INCI: Disodium PEG-5 Laurylcitrate Sulfosuccinate; Sodium Laureth Sulfate) | 7.50 |
| Water | 59.60 |
| TEGO ® Betain F 50, Evonik Goldschmidt GmbH, 38% strength, (INCI: Cocamidopropyl Betaine) | 9.00 |
| TEGO ® Betain 810, Evonik Goldschmidt GmbH, 38% strength, (INCI: Capryl/Capramidopropyl Betaine) | 4.00 |
| Polyquaternium-7, Nalco, (INCI: Merquat 550) | 0.50 |
| ANTIL ® 200, Evonik Goldschmidt GmbH, (INCI: PEG-200 Hydrogenated Glyceryl Palmate; PEG-7 Glyceryl Cocoate) | 1.80 |
| Preservative | 0.30 |

TABLE 5-18

| Formulation Example 18, body cleaning composition | | |
|---|---|---|
| A | TEXAPON ® NSO, Cognis, 28% strength, (INCI: Sodium Laureth Sulfate) | 30.00 |
| | Cap01 | 0.50 |
| | ABIL ® B 8832, Evonik Goldschmidt GmbH, (INCI: Bis-PEG/PPG-20/20 Dimethicone) | 0.30 |
| | Perfume | 0.30 |
| B | Water | 53.00 |
| | TEGOCEL ® fluid HPM 4000, Evonik Goldschmidt GmbH, (INCI: Hydroxypropyl Methylcellulose) | 1.20 |
| | Citric Acid Monohydrate | 0.50 |
| | REWOTERIC ® AM C, Evonik Goldschmidt GmbH, 32% strength, (INCI: Sodium Cocoamphoacetate) | 10.00 |
| | Cutina TS, Cognis (INCI: PEG-3 Distearate) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.60 |
| | Preservative | 0.60 |
| | Citric Acid, 30% strength | q.s. |

TABLE 5-19

| Formulation Example 19, body cleansing foam | |
|---|---|
| TEXAPON ® NSO, Cognis, 28% strength (INCI: Sodium Laureth Sulfate) | 14 |
| Perfume | 0.3 |
| Cap01 | 0.2 |
| REWOTERIC ® AM C, Evonik Goldschmidt GmbH, 32% strength (INCI: Sodium Cocoamphoacetate) | 8 |
| Water | 75.3 |
| TEGOCEL ® HPM 50, Evonik Goldschmidt GmbH (INCI: Hydroxypropyl Methylcellulose) | 0.5 |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1 |
| Panthenol, BASF, (INCI: D-Panthenol USP) | 0.2 |
| Citric Acid Monohydrate | 0.5 |

TABLE 5-20

| Formulation Example 20, rinse-off conditioner | |
|---|---|
| Water | 90.20 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| Cap01 | 0.80 |
| TEGO ® Alkanol 16, Evonik Goldschmidt GmbH (INCI: Cetyl Alcohol) | 5.00 |
| Preservative, Perfume | q.s. |

TABLE 5-21

| Formulation Example 21, rinse-off conditioner | |
|---|---|
| Water | 90.20 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| Cap01 | 0.80 |
| TEGO ® Alkanol 18, Evonik Goldschmidt GmbH, (INCI: Stearyl Alcohol) | 5.00 |
| Preservative, Perfume | q.s. |

TABLE 5-22

| Formulation Example 22, rinse-off conditioner | |
|---|---|
| Water | 89.20 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| Cap01 | 0.80 |
| TEGO ® Alkanol 1618, Evonik Goldschmidt GmbH (INCI: Cetearyl Alcohol) | 5.00 |
| DC 949, Dow Corning, (INCI: Amodimethicone) | 1.00 |
| Preservative, Perfume | q.s. |

TABLE 5-23

| Formulation Example 23, rinse-off conditioner | |
|---|---|
| Water | 89.20 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| Cap01 | 0.80 |
| TEGO ® Alkanol 1618, Evonik Goldschmidt GmbH (INCI: Cetearyl Alcohol) | 5.00 |
| DC 1503 Fluid, Dow Corning, (INCI: Dimethicone, Dimethiconol) | 1.00 |
| Preservative, Perfume | q.s. |

TABLE 5-24

| Formulation Example 24, turbid conditioning shampoo | |
|---|---|
| TEXAPON ® NSO, Cognis, 28% strength (INCI: Sodium Laureth Sulfate) | 32.00 |
| ANTIL ® 200, Evonik Goldschmidt GmbH (INCI: PEG-200 Hydrogenated Glyceryl Palmate; PEG-7 Glyceryl Cocoate) | 2.00 |
| Cap01 | 1.00 |
| Perfume | 0.25 |
| Water | 53.25 |
| Polymer JR 400, Amerchol (INCI: Polyquaternium-10) | 0.20 |
| TEGO ® Betain F 50, Evonik Goldschmidt GmbH, 38% strength (INCI: Cocamidopropyl Betaine) | 8.00 |
| DC1503 Fluid, Dow Corning, (INCI: Dimethicone, Dimethiconol) | 1.00 |
| TEGO ® Pearl N 300, Evonik Goldschmidt GmbH (INCI: Glycol Distearate; Laureth-4; Cocamidopropyl Betaine) | 2.00 |
| NaCl | 0.30 |
| Preservative | q.s. |

TABLE 5-25

| Formulation Example 25, conditioning anti-dandruff shampoo | | |
|---|---|---|
| A | TEGIN ® G 1100 Pellets, Evonik Goldschmidt GmbH, (INCI: Glycol Distearate) | 3.00 |
| | TEXAPON ® NSO, Cognis, 28% strength (INCI: Sodium Laureth Sulfate) | 40.0 |
| B | Perfume | 0.30 |
| | Zinc-Pyrion NF, WeylChem, 48% strength (INCI: Zinc Pyrithione) | 2.00 |
| | ABIL ® Quat 3272, Evonik Goldschmidt GmbH, (INCI: Quaternium-80) | 1.00 |
| C | Water | 36.7 |
| | TEGO ® Carbomer 341 ER, Evonik Goldschmidt GmbH, (INCI: Acrylates/C10-30 Alkyl Acrylate Crosspolymer) | 0.20 |
| | Polymer JR 400, Amerchol, (INCI: Polyquaternium-10) | 0.30 |
| | NaOH, 25% strength | 0.30 |
| D | Rewoteric AM B U 185 ®, Evonik Goldschmidt GmbH, (INCI: Undecylenamidopropyl Betaine) | 12.5 |
| | Cap01 | 3.70 |
| | Preservative | q.s |

TABLE 5-26

| Formulation Example 26, conditioning anti-dandruff shampoo | | |
|---|---|---|
| A | TEGIN ® G 1100 Pellets, Evonik Goldschmidt GmbH, (INCI: Glycol Distearate) | 3.00 |
| | TEXAPON ® NSO, Cognis, 28% strength (INCI: Sodium Laureth Sulfate) | 40.0 |
| B | Perfume | 0.30 |
| | Crinipan AD, Haarmann & Reimer Fragrance GmbH (INCI: Climbazol) | 0.30 |
| | ABIL ® Quat 3272, Evonik Goldschmidt GmbH, (INCI: Quaternium-80) | 1.00 |
| C | Water | 38.4 |
| | TEGO ® Carbomer 341 ER, Evonik Goldschmidt GmbH, (INCI: Acrylates/C10-30 Alkyl Acrylate Crosspolymer) | 0.20 |
| | Polymer JR 400, Amerchol, (INCI: Polyquaternium-10) | 0.30 |
| | NaOH, 25% strength | 0.30 |
| D | Rewoteric AM B U 185 ®, Evonik Goldschmidt GmbH, (INCI: Undecylenamidopropyl Betaine) | 12.5 |
| | Cap01 | 3.70 |
| | Preservative | q.s |

TABLE 5-27

| Formulation Example 27, conditioning anti-dandruff shampoo | | |
|---|---|---|
| A | TEGIN ® G 1100 Pellets, Evonik Goldschmidt GmbH, (INCI: Glycol Distearate) | 3.00 |
| | TEXAPON ® NSO, Cognis, 28% strength (INCI: Sodium Laureth Sulfate) | 40.0 |
| B | Perfume | 0.30 |
| | Zinc-Pyrion NF, WeylChem, 48% strength (INCI: Zinc Pyrithione) | 2.00 |
| | ABIL ® Quat 3272, Evonik Goldschmidt GmbH, (INCI: Quaternium-80) | 1.00 |
| C | Water | 36.4 |
| | TEGO ® Carbomer 140, Evonik Goldschmidt GmbH, (INCI: Carbomer) | 0.50 |
| | Polymer JR 400, Amerchol, (INCI: Polyquaternium-10) | 0.30 |
| | NaOH, 25% strength | 0.30 |
| D | Rewoteric AM B U 185 ®, Evonik Goldschmidt GmbH, (INCI: Undecylenamidopropyl Betaine) | 12.5 |
| | Cap01 | 3.70 |
| | Preservative | q.s |

TABLE 5-28

| Formulation Example 28, conditioning anti-dandruff shampoo | | |
|---|---|---|
| A | TEGIN ® G 1100 Pellets, Evonik Goldschmidt GmbH, (INCI: Glycol Distearate) | 3.00 |
| | TEXAPON ® NSO, Cognis, 28% strength (INCI: Sodium Laureth Sulfate) | 40.0 |
| B | Perfume | 0.30 |
| | Piroctone Olamine, Clariant (INCI: Octoprirox) | 0.30 |
| | ABIL ® Quat 3272, Evonik Goldschmidt GmbH, (INCI: Quaternium-80) | 1.00 |
| C | Water | 38.4 |
| | TEGO ® Carbomer 341 ER, Evonik Goldschmidt GmbH, (INCI: Acrylates/C10-30 Alkyl Acrylate Crosspolymer) | 0.20 |
| | Polymer JR 400, Amerchol, (INCI: Polyquaternium-10) | 0.30 |
| | NaOH, 25% strength | 0.30 |
| D | Rewoteric AM B U 185 ®, Evonik Goldschmidt GmbH, (INCI: Undecylenamidopropyl Betaine) | 12.5 |
| | Cap01 | 3.70 |
| | Preservative | q.s |

The invention claimed is:

1. A composition comprising a mixture which comprises at least one isostearamide, at least one glycerol ester and water, wherein the isostearamide is an amide condensation product of isostearic acid with 1-amino-2-propanol, and said isostearamide is present in an amount of 50 to 95% by weight of the mixture.

2. The composition according to claim 1, wherein the isostearamide is present in an amount of 70 to 90% by weight of the mixture.

3. The composition according to claim 1, wherein the mixture comprises, as the at least one glycerol ester, glycerol laurate.

4. The composition according to claim 1, wherein the fraction of the at least one glycerol ester in the mixture is from 1 to 45% by weight, based on the total weight of the mixture.

5. The composition according to claim 1, wherein the fraction of water in the mixture is from 1 to 15% by weight, based on the total weight of the mixture.

6. A thickening composition consisting of at least one isostearamide, at least one glycerol ester, and water, wherein the isostearamide is an amide condensation product of isostearic acid with 1-amino-2-propanol.

7. The thickening composition according to claim 6, wherein said at least one glycerol ester is glycerol laurate and/or glycerol caprylate/caprate.

8. The thickening composition according to claim 7, wherein the fraction of water in the composition is greater than 35% by weight.

9. A shampoo, conditioner, shower gel, body cleaning composition or skin cleaning composition comprising the composition according to claim 1.

10. A process for producing the composition according to claim 7, comprising mixing the composition with one or more further components.

11. The process according to claim 10, wherein the composition is mixed with water and one or more further components, where at least sufficient water is mixed in for the fraction of the water in the overall composition to be greater than 35% by weight.

12. The composition according to claim 3, wherein said glycerol laurate is glycerol monolaurate.

13. The thickening composition according to claim 6, wherein said isostearamide is present in an amount of 50 to 95% by weight of the composition.

14. The thickening composition according to claim 6, wherein said isostearamide is present in an amount of 70 to 90% by weight of the composition.

15. The thickening composition according to claim 6, wherein said at least one glycerol ester is present in an amount of 1 to 45% by weight of the composition.

* * * * *